(12) United States Patent
Subilski

(10) Patent No.: US 11,123,472 B2
(45) Date of Patent: Sep. 21, 2021

(54) VACUUM ASSISTED SKIN PENETRATING APPLIANCE WITH EXTERNAL INTERFACE

(71) Applicant: VIADERM, LLC, Ann Arbor, MI (US)

(72) Inventor: Susan Subilski, St. Paul, MN (US)

(73) Assignee: VIADERM, LLC, Plymouth, MI (US)

( * ) Notice: Subject to any disclaimer, the term of this patent is extended or adjusted under 35 U.S.C. 154(b) by 400 days.

(21) Appl. No.: 15/555,952

(22) PCT Filed: Mar. 4, 2016

(86) PCT No.: PCT/US2016/020895
§ 371 (c)(1),
(2) Date: Sep. 5, 2017

(87) PCT Pub. No.: WO2016/141291
PCT Pub. Date: Sep. 9, 2016

(65) Prior Publication Data
US 2018/0043069 A1     Feb. 15, 2018

Related U.S. Application Data

(60) Provisional application No. 62/128,280, filed on Mar. 4, 2015.

(51) Int. Cl.
*A61M 1/00* (2006.01)
*A61M 39/02* (2006.01)
*A61M 25/02* (2006.01)

(52) U.S. Cl.
CPC .............. *A61M 1/90* (2021.05); *A61M 25/02* (2013.01); *A61M 39/0247* (2013.01);
(Continued)

(58) Field of Classification Search
CPC .............. A61M 25/02; A61M 39/0247; A61M 2025/0233; A61M 2039/0279; A61M 2039/0273; A61M 2039/0261
See application file for complete search history.

(56) References Cited

U.S. PATENT DOCUMENTS 3,765,420 A * 10/1973 Felczak ................. A61B 17/32
604/117
4,092,983 A  6/1978 Slivenko
(Continued)

OTHER PUBLICATIONS

Supplementary European Search Report dated Oct. 30, 2018 for European Application No. 16759576 filed Mar. 4, 2016.
(Continued)

*Primary Examiner* — Tatyana Zalukaeva
*Assistant Examiner* — Jessica R Arble
(74) *Attorney, Agent, or Firm* — Blue Filament Law PLLC

(57) ABSTRACT

A system and method for a modular external interface for a skin penetrating appliance is provided. The modular device prevents internalization of bacteria, other infectious agents, or other unwanted materials from entering the access point for a catheter, Steinman pin, Kirschner wires, or other percutaneous instruments. The modular external interface provides for the hermaticity in the vicinity of the skin-appliance interface with fluid exudate or transudate egressing from the vicinity of the skin-appliance interface. The modular external interface forms a hermetic seal with the external neck of an implanted appliance with a locking feature that joins the main body of the modular external interface together around the neck of the appliance. The modular external interface provides mechanical stability to an implanted appliance so as to speed healing around a semi-permanent implanted appliance, as well as connection points for vacuum lines and drive lines for the insertion of medical devices.

21 Claims, 18 Drawing Sheets

(52) U.S. Cl.
CPC ............... *A61M 2025/0233* (2013.01); *A61M 2039/0261* (2013.01); *A61M 2039/0273* (2013.01); *A61M 2039/0279* (2013.01)

(56) References Cited

U.S. PATENT DOCUMENTS

| | | | |
|---|---|---|---|
| 4,417,888 A | 11/1983 | Cosentino et al. | |
| 4,634,422 A | 1/1987 | Kantrowitz et al. | |
| 4,668,222 A | 5/1987 | Poirier | |
| 4,886,502 A * | 12/1989 | Poirier | A61M 1/285 604/175 |
| 5,059,186 A | 10/1991 | Yamamoto et al. | |
| 5,120,313 A | 6/1992 | Elftman | |
| 5,250,025 A | 10/1993 | Sosnowski et al. | |
| 5,685,859 A * | 11/1997 | Kornerup | A61M 25/02 604/179 |
| 5,814,058 A | 9/1998 | Carlson et al. | |
| 5,833,666 A | 11/1998 | Davis et al. | |
| 5,997,524 A | 12/1999 | Burbank et al. | |
| 6,503,228 B1 | 1/2003 | Li et al. | |
| 7,338,482 B2 | 3/2008 | Lockwood et al. | |
| 7,704,225 B2 | 4/2010 | Kantrowitz | |
| 7,988,673 B2 | 8/2011 | Wright et al. | |
| 2002/0042593 A1* | 4/2002 | Mickley | A61M 5/00 604/102.01 |
| 2004/0243073 A1* | 12/2004 | Lockwood | A61M 1/0084 604/313 |
| 2005/0085795 A1 | 4/2005 | Lockwood et al. | |
| 2008/0051828 A1* | 2/2008 | Sample | A61B 17/085 606/213 |
| 2010/0200076 A1* | 8/2010 | Hieb | A61M 5/16827 137/15.04 |
| 2011/0106014 A1* | 5/2011 | Helm, Jr. | A61M 25/02 604/178 |
| 2012/0310181 A1* | 12/2012 | Kantrowitz | A61M 39/0247 604/264 |
| 2013/0006186 A1 | 1/2013 | Kantrowitz et al. | |
| 2014/0276454 A1* | 9/2014 | Kuiken | A61M 39/0247 604/246 |
| 2014/0330224 A1* | 11/2014 | Albert | A61F 13/022 604/319 |
| 2014/0343520 A1 | 11/2014 | Bennett et al. | |

OTHER PUBLICATIONS

International Search Report dated Jul. 25, 2016 for International Application No. PCT/US2016/020895 filed Mar. 4, 2016.

* cited by examiner

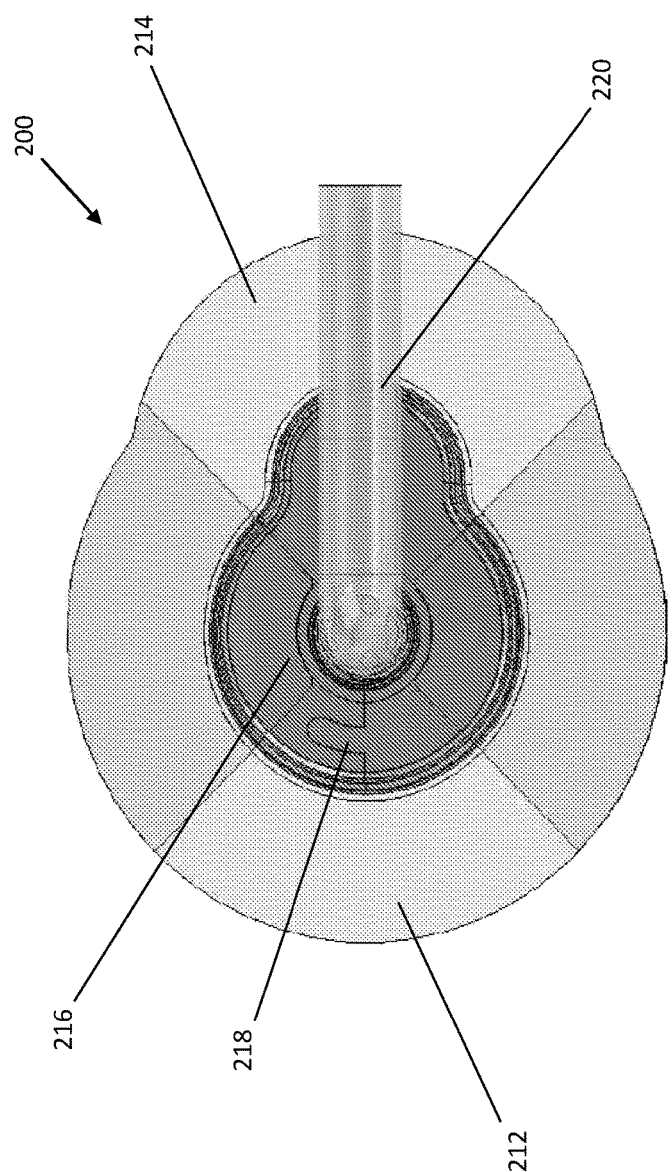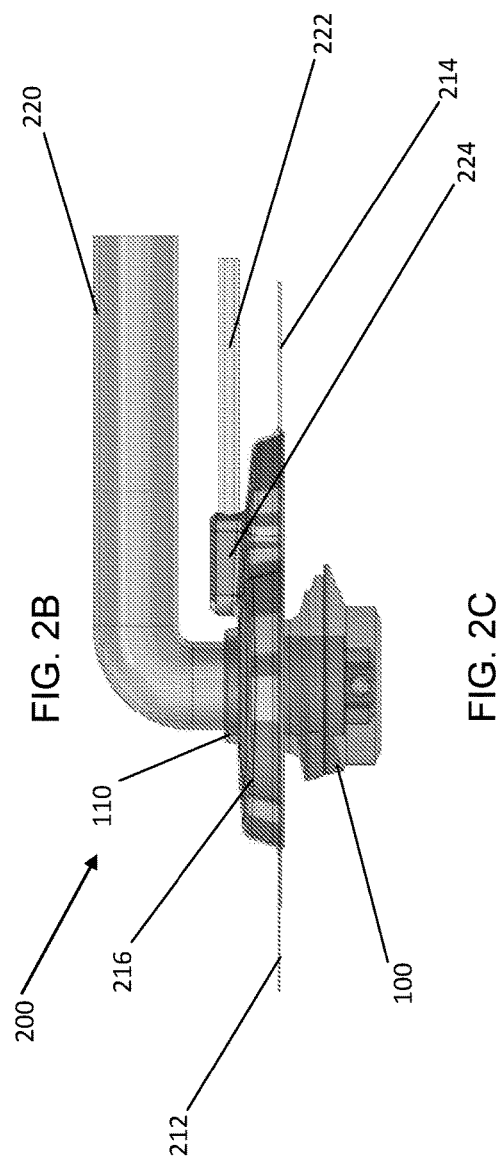

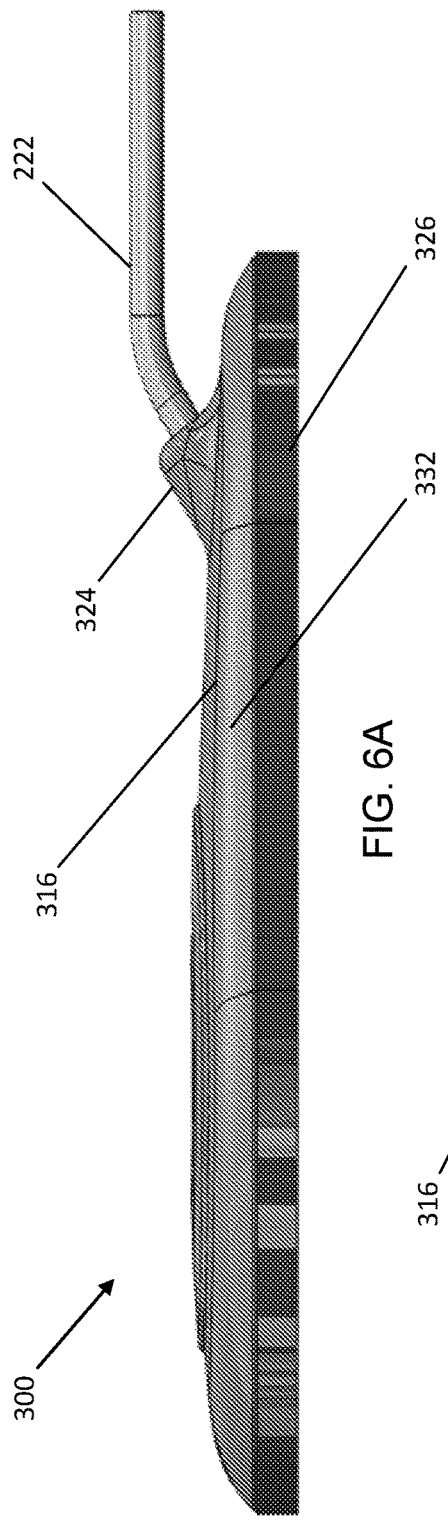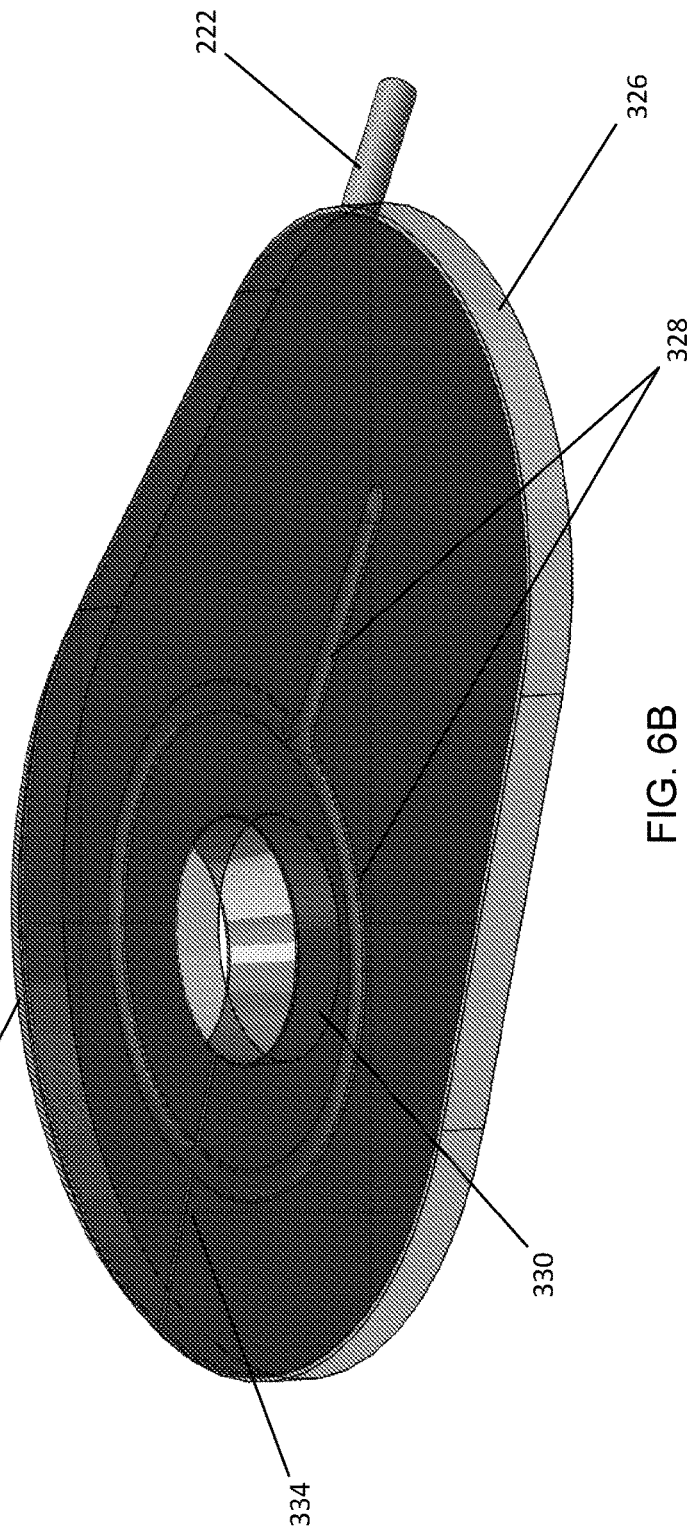
FIG. 6A
FIG. 6B (Section A-A)

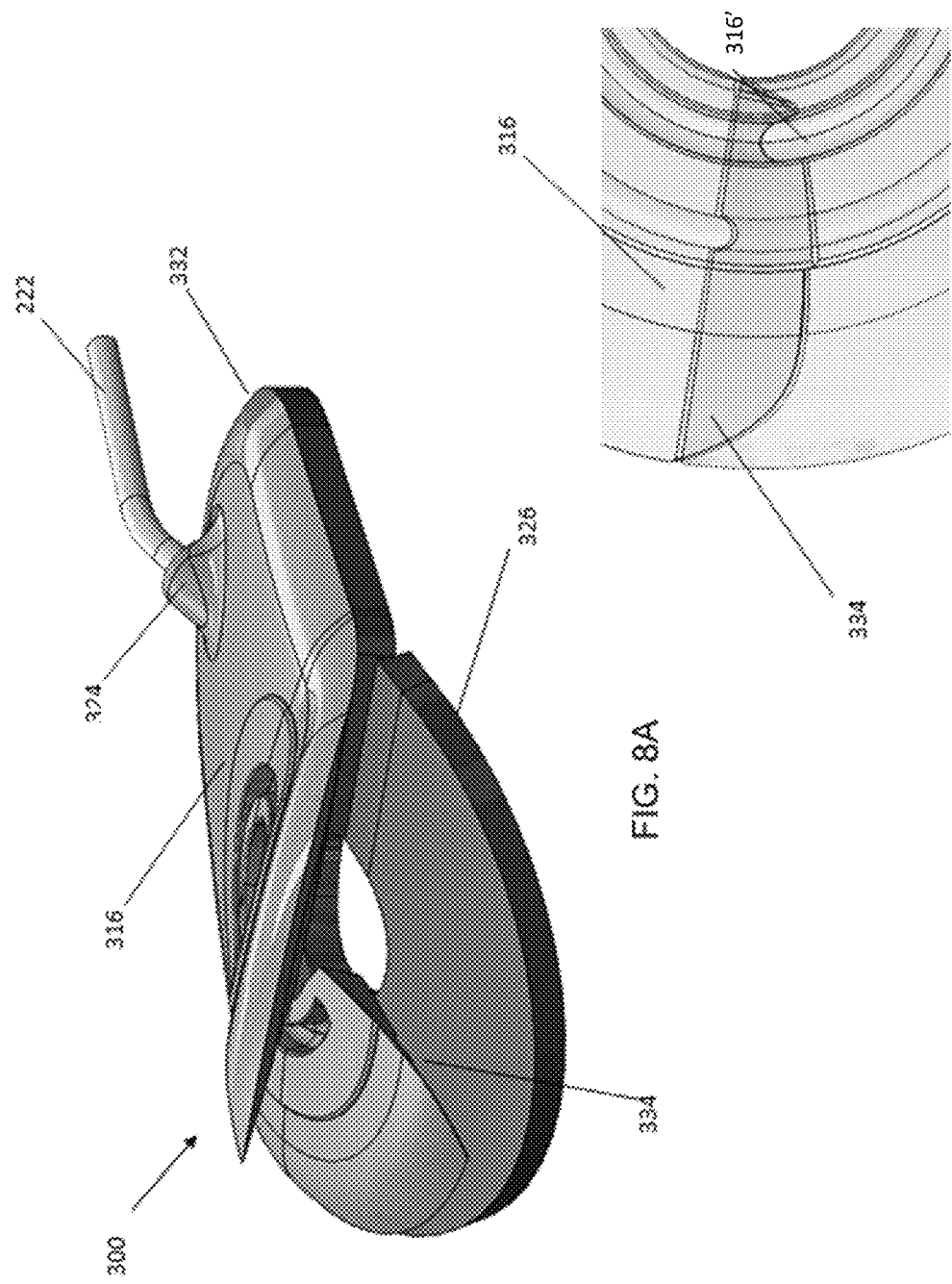

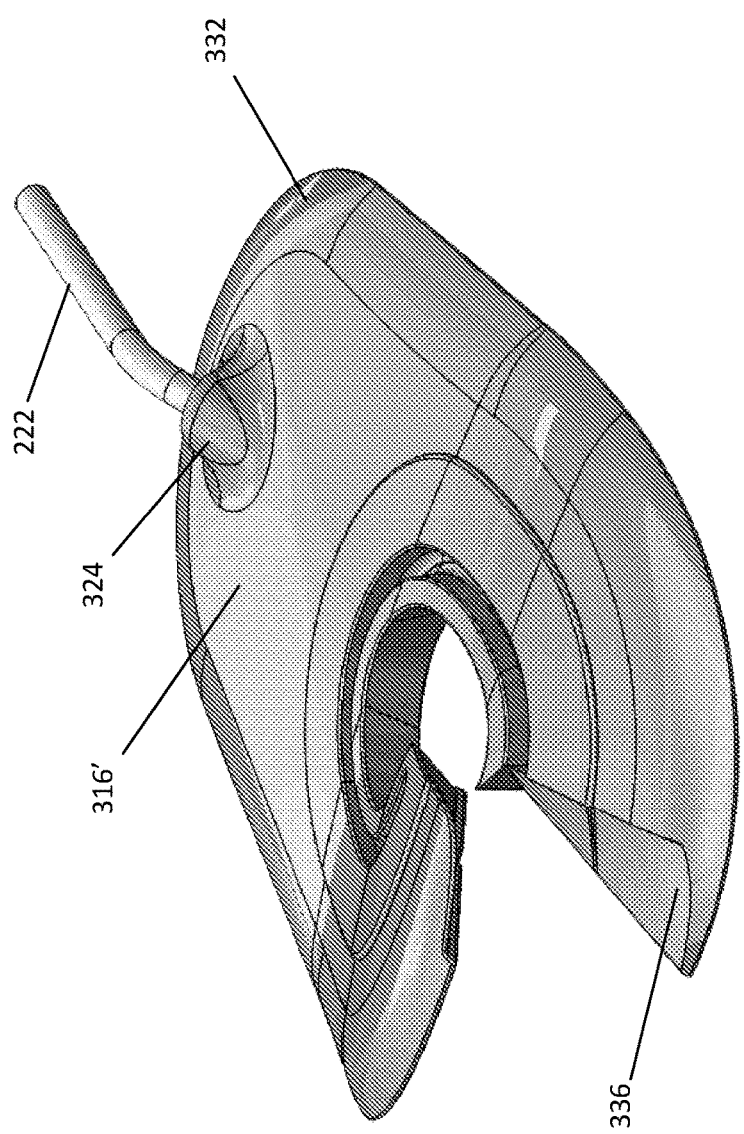
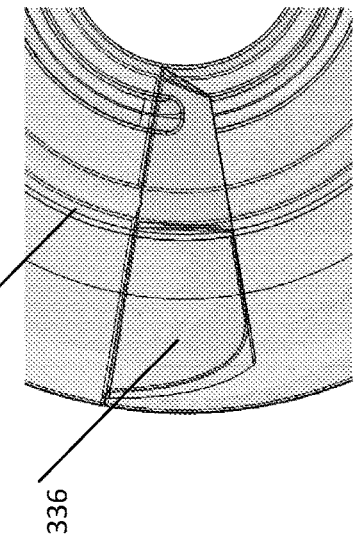
FIG. 9A
FIG. 9B

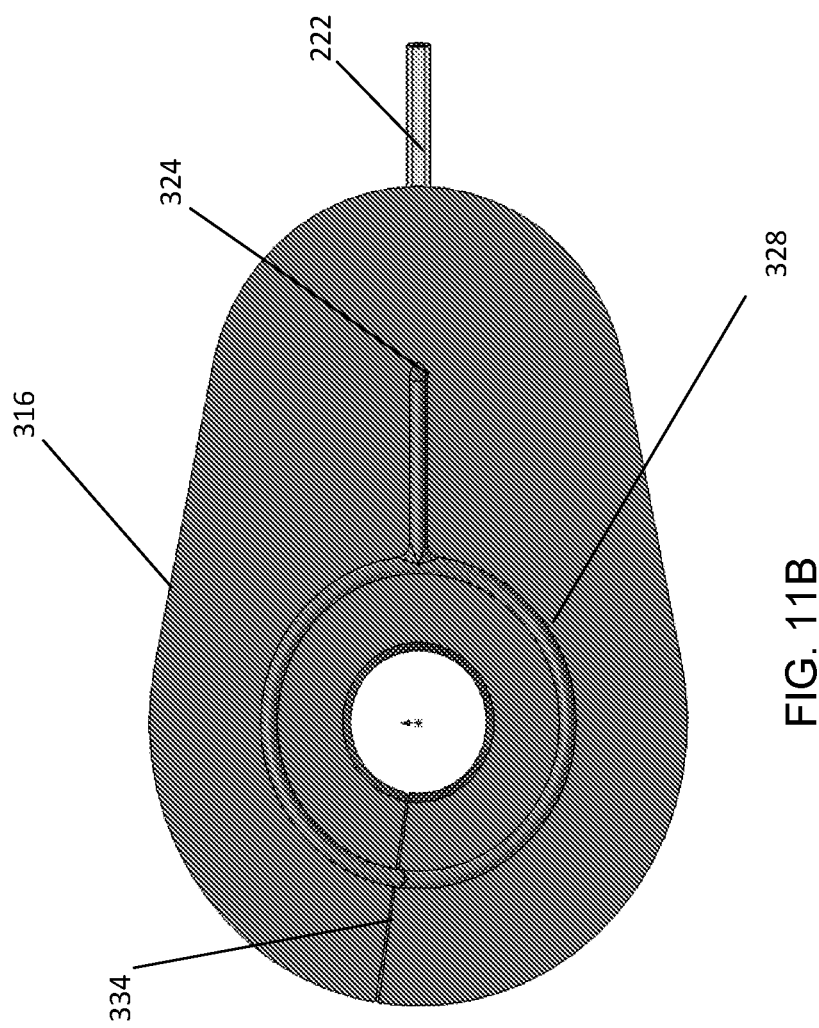
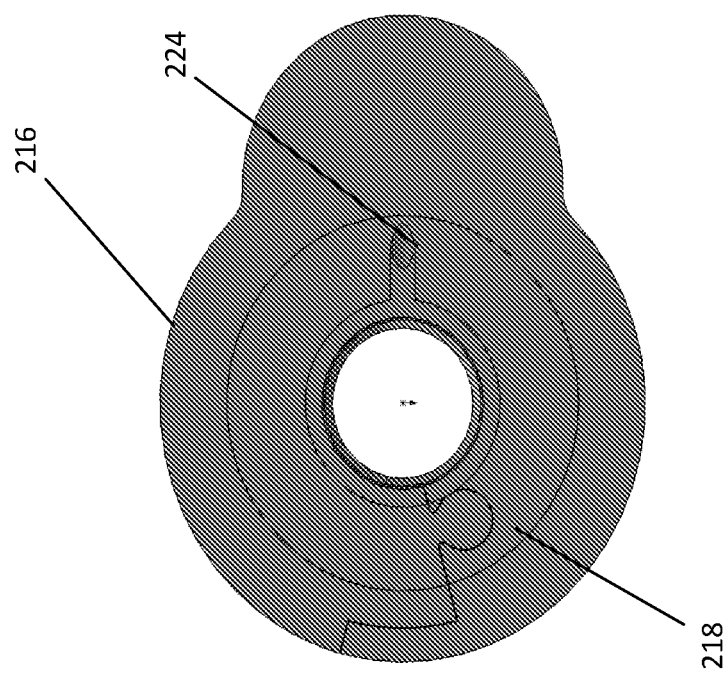
FIG. 11B
FIG. 11A

VACUUM ASSISTED SKIN PENETRATING APPLIANCE WITH EXTERNAL INTERFACE

CROSS REFERENCE TO RELATED APPLICATIONS

This application claims priority benefit of U.S. Provisional Application Ser. No. 62/128,280 filed 4 Mar. 2015; the contents of which are hereby incorporated by reference.

FIELD OF THE INVENTION

The present invention in general relates to medical devices and systems and in particular to percutaneous access devices for preventing infection at the site of cutaneous access. More specifically, the invention provides processes and devices for preventing internalization of bacteria, other infectious agents, or other unwanted materials from entering the access point for a catheter, Steinman pin, Kirschner wires, or other percutaneous instruments.

BACKGROUND OF THE INVENTION

A common problem associated with implantation of a cutaneous access device (PAD) or other skin penetrating appliance is skin regeneration about the periphery of the appliance to form an immunoprotective seal against infection. New cell growth and maintenance is typically frustrated by the considerable mechanical forces exerted on the interfacial layer of cells. In order to facilitate skin regeneration about the exterior of the appliance, subject cells are often harvested and grown in culture onto appliance surfaces for several days prior to implantation in order to allow an interfacial cell layer to colonize appliance surfaces in advance of implantation. Unfortunately, cell culturing has met with limited acceptance owing to the need for a cell harvesting surgical procedure preceding the implantation procedure. Additionally, maintaining tissue culture integrity is also a complex and time-consuming task.

A related context in which cell growth is needed is wound healing, with DACRON® based random felt meshes have been used to promote cell regrowth in the vicinity of a wound, such felts have uncontrolled pore sizes that harbor bacterial growth pockets.

U.S. Pat. No. 7,704,225 to Kantrowitz solves many of these aforementioned problems by providing cell channeling contours, porous biodegradable polymers and the application of vacuum to promote cellular growth towards the surface the neck of a PAD. The facilitating of rapid cellular colonization of a PAD neck allows the subject to act as their own cell culture facility and as such affords more rapid stabilization of the PAD, and lower incidence of separation and infection.

FIG. 1 depicts a PAD generally at 100 as shown in U.S. application Ser. No. 13/416,546 to Kantrowitz. A cap 102 is formed of a material such as silicone, a polymer or a metal and serves to keep debris from entering the device 100. Preferably, the cap 102 is remote from the surface of the epidermis E. The medical appliance 34 depicted as a catheter and vacuum or hydrodynamic draw tubing 104 pass through complementary openings 106 and 108, respectively formed in the cap 102. The tubing 104 provides fluid communication between a vacuum or hydrodynamic draw source 22 and an inner sleeve 12d. The inner sleeve 12d is characterized by a large and rigid pore matrix 18 in fluid communication to a vacuum source 22 such that the source 22 draws (arrow 22D) tissue fluid and fibroblasts 21 into the sleeve 12d.

Sleeve 12d has a surface 24 that is optionally nanotextured to promote fibroblast adhesion. The surface 24 is optionally decorated with a pattern of contoured cell-conveying channels. It is appreciated that inner sleeve 12d optionally includes matrix 26 thereover, a coating substance 27, or a combination thereof. The coating 27 is appreciated to need not cover the entire surface 24. The tissue contacting surface 29 of substance 27 is optionally nanotextured. A flange 112 is provided to stabilize the implanted device 100 within the subcuteanous layer S. A flange 112 is constructed from materials and formed by methods conventional to the art. For example, those detailed in U.S. Pat. Nos. 4,634,422; 4,668,222; 5,059,186; 5,120,313; 5,250,025; 5,814,058; 5,997,524; and 6,503,228.

While there have been many advances in skin penetrating appliance designs for preventing infection at the site of skin access, there continues to be a need for improved external interfaces for implanted appliances.

SUMMARY OF THE INVENTION

A modular external interface includes a main body with an aperture configured to form a collar seal about an external neck portion of a skin penetrating appliance. The modular external interface has a portal configured for insertion of a vacuum tube, and at least one driveline inserted through the aperture and into the appliance.

A modular external interface includes a main body with an aperture configured to form a collar seal about an external neck portion of a skin penetrating appliance, where a slit extends outward from the aperture. A portal configured for insertion of a vacuum tube is on the main body, where the portal is in fluid communication with a vacuum channel on a bottom side of the main body. A foam layer is positioned under the main body, and at least one driveline inserted through the aperture and into the appliance.

A process of using the modular external interface to form a collar seal about an external neck portion of a skin penetrating appliance is provided that includes placing the modular external interface over the external neck portion of the skin penetrating appliance implanted in a subject, and applying a medical dressing to secure the modular external interface to the patient's skin.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIGS. 2A-2C are perspective views of a modular external interface seal for a PAD appliance in accordance with an embodiment of the invention;

FIGS. 6A and 6B are perspective views of a modular external interface seal for a PAD appliance in accordance with an embodiment of the invention;

FIGS. 8A and 8B illustrate a simple split in the main body in accordance with embodiments of the invention;

FIGS. 9A and 9B illustrate a slanted slit in accordance with embodiments of the invention;

FIGS. 11A and 11B are a comparison of the modular external interface as shown in FIGS. 2A and 6A in accordance with an embodiment of the invention;

The detailed description explains the preferred embodiments of the invention.

DESCRIPTION OF THE INVENTION

The present invention has utility as a system and method for a modular external interface for a skin penetrating appliance. The present invention also provides processes and devices for preventing internalization of bacteria, other infectious agents, or other unwanted materials from entering the access point for a catheter, Steinman pin, Kirschner wires, or other percutaneous instruments.

While such an appliance is depicted in the accompanying figures as an embedded percutaneous access device (PAD), it is appreciated that it is applicable to a variety of such appliances including a catheter, a Steinman pin, and a Kirschner wire. Embodiments of the modular external interface provide for the hermaticity in the vicinity of the skin-appliance (PAD) interface with fluid exudate or transudate egressing from the vicinity of the skin-PAD interface. Embodiments of the modular external interface form a hermetic seal with the external neck of an implanted PAD with a locking feature that joins the main body of the modular external interface together around the neck of the PAD. Embodiments of the modular external interface provide additional mechanical stability to an implanted PAD so as to speed healing around a semi-permanent implanted PAD, as well as connection points for vacuum lines and at least one drive line for the insertion of medical devices.

Figure 2A:
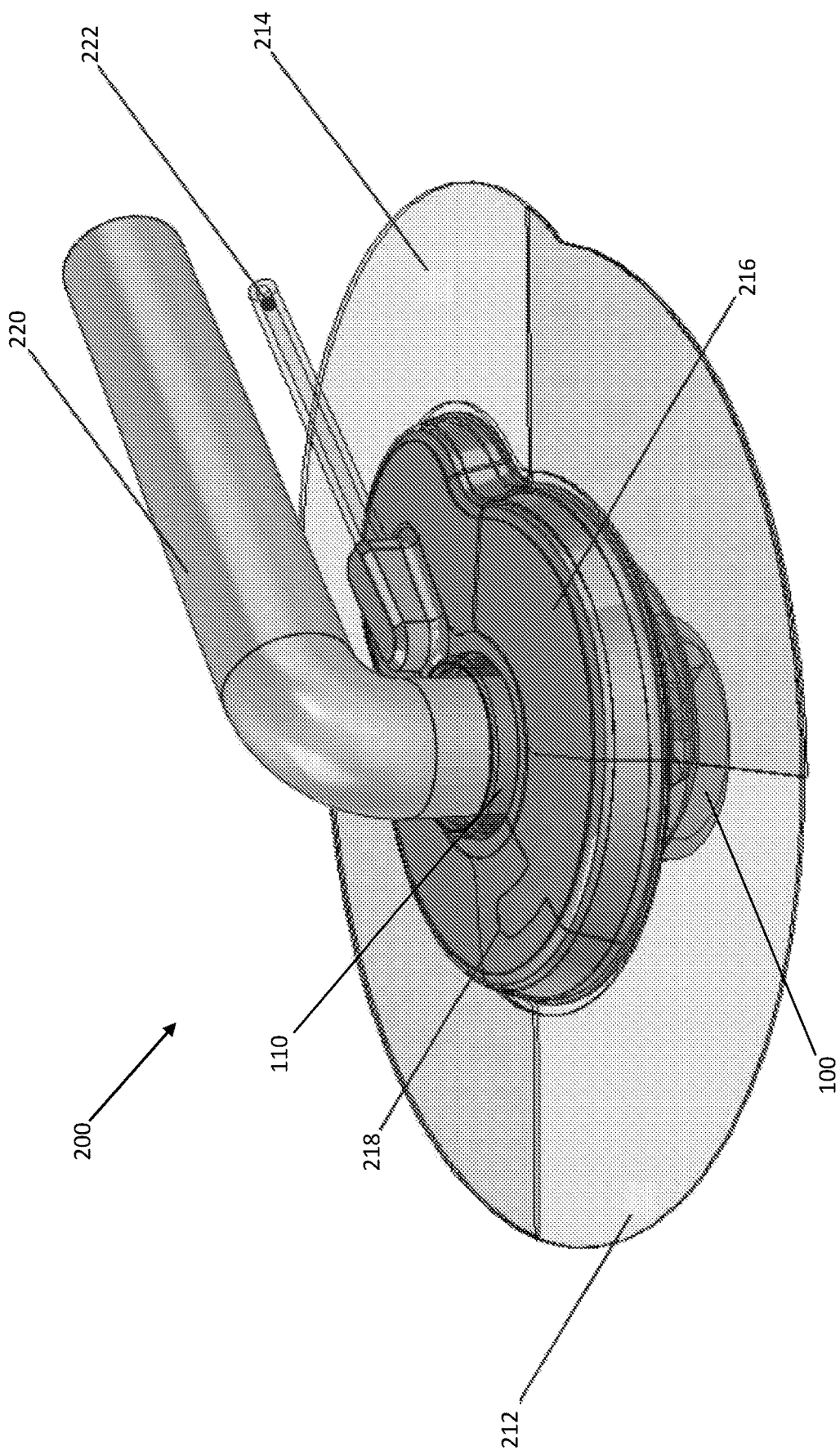
Figure 3:
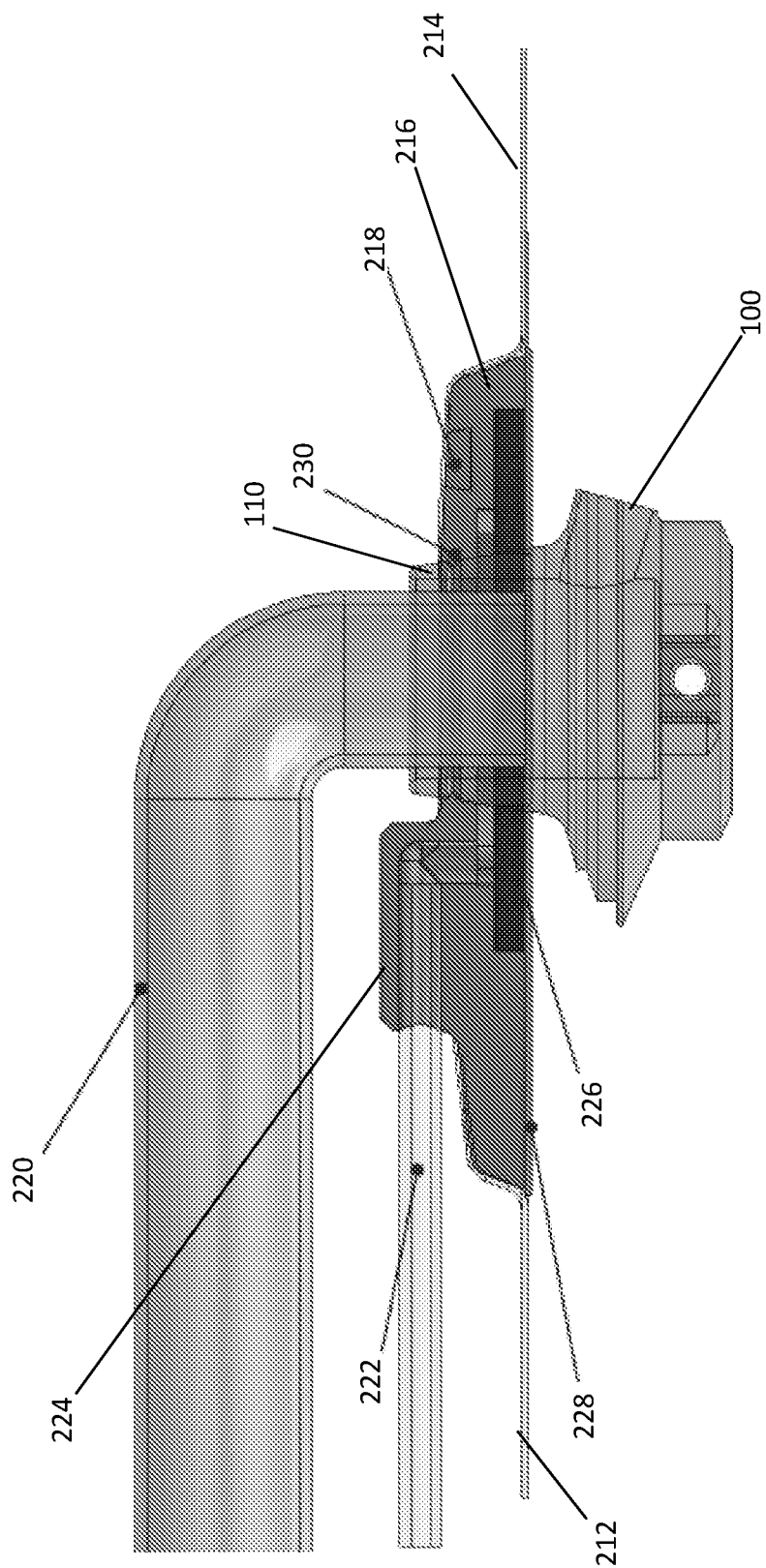
FIG. 3 illustrates a side cross sectional view of FIG. 2C according to an embodiment of the invention.

Referring now to the figures, FIGS. 2A-2C illustrate an embodiment of an inventive modular external interface housing 200 coupled to a PAD 100. The modular external interface 200 forms a collar about the neck 110 of the PAD 100 with the main body 216 with a locking feature 218, such as a male extension that engages a female receptacle or cavity as a mechanical overlap connection. In a specific embodiment the main body 216 is made of silicone. As best shown in FIG. 3, the collar seal between the main body 216 and the neck 110 of the PAD 100 forms a hermetic seal with a gasket 230, which in a specific embodiment is a flexible gasket integrated into the main body 216. In a specific embodiment the gasket 230 may be a floating gasket. The stabilization of the PAD 100 within the skin to form a germ-free barrier requires subject cells to grow onto the neck surfaces 16 of the PAD 100 adjacent to the subject's epidermis E. The neck surface region 16 is adapted to promote growth of autologous fibroblast cells thereon. A suitable exterior side surface substrate for fibroblast growth is a nanotextured polycarbonate (LEXAN®).

The modular external interface 200 is secured and sealed to an outer layer of a patient's skin with a medical dressing. In a specific embodiment the medical dressing is a preform patterned and shaped to conform to the exterior of the modular external interface 200. In a specific embodiment the medical dressing preform may be in two halves (212 214) that overlap. In a specific embodiment the medical dressing preform may be transparent. In a specific embodiment the medical dressing preform may be made of Tegaderm™ manufactured by Minnesota Mining and Manufacturing Company.

Figure 4:
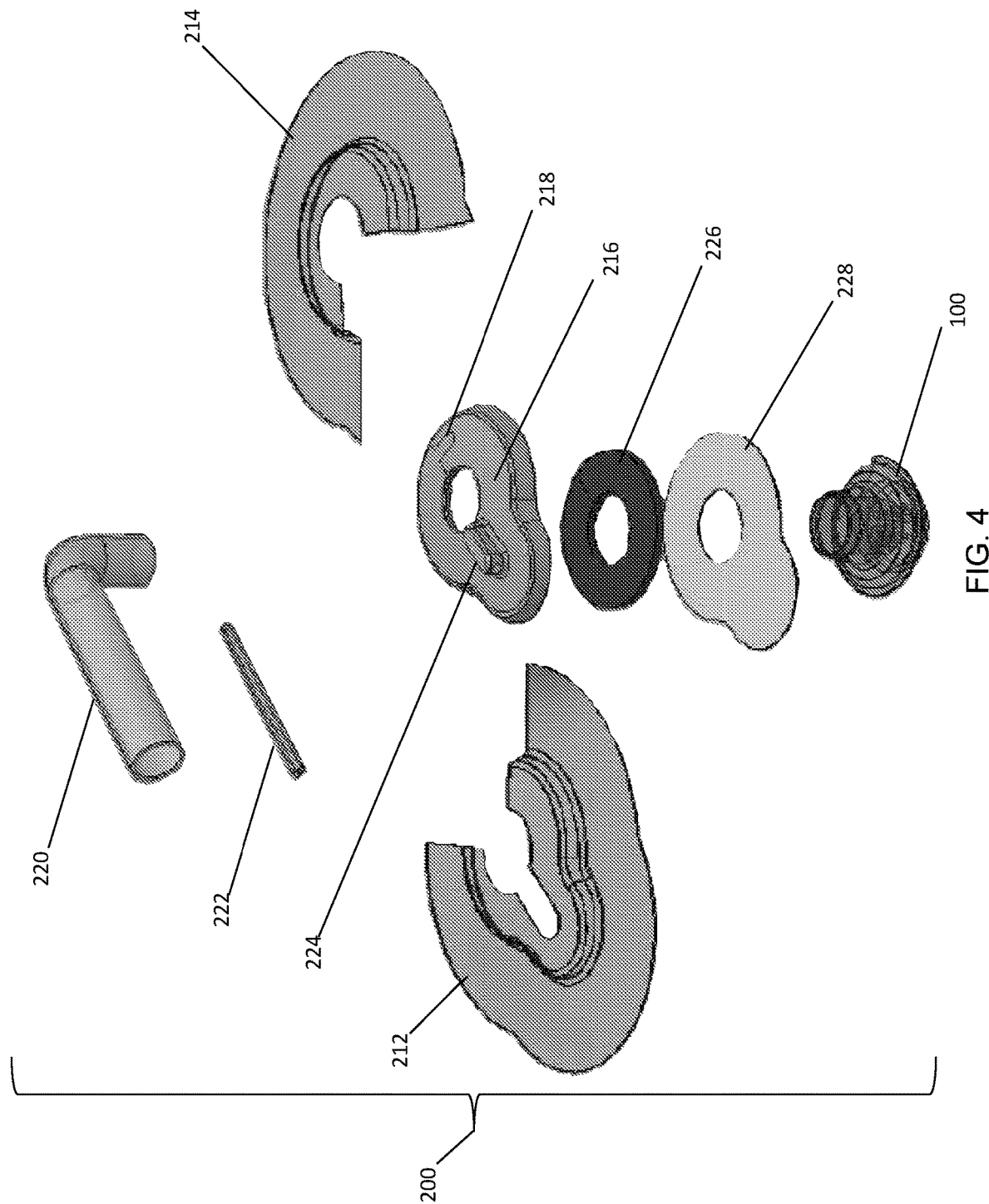
FIG. 4 is an exploded view of the modular external interface for a percutaneous access device according to an embodiment of the invention.
Figure 5:
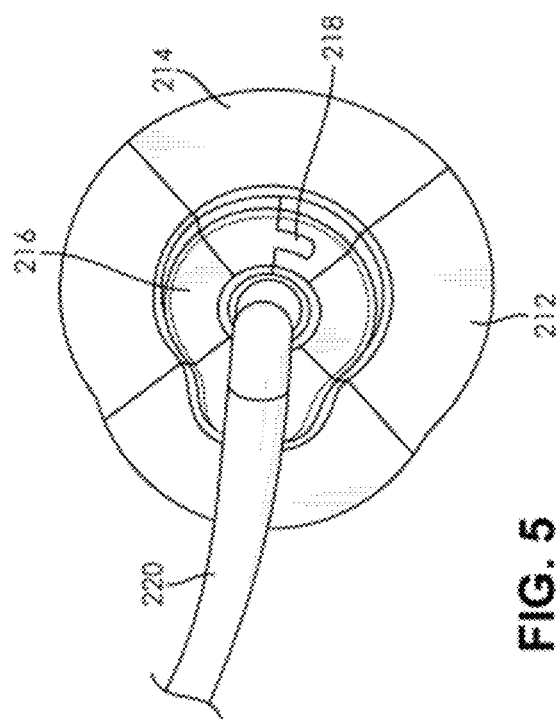
FIG. 5 illustrates the modular external interface attached to a patient with an underlying PAD in accordance with an embodiment of the invention.

The modular external interface 200 has a central opening adapted at least one drive line 220 for insertion into a PAD, and a portal 224 for a vacuum line 222. As best shown in FIGS. 3 and 4 a skin protection layer 228 and a foam disc 226 are positioned in the interior of the modular external interface 200. FIG. 5 illustrates the modular external interface attached to a patient with an underlying PAD in accordance with an embodiment of the invention.

Figure 1:
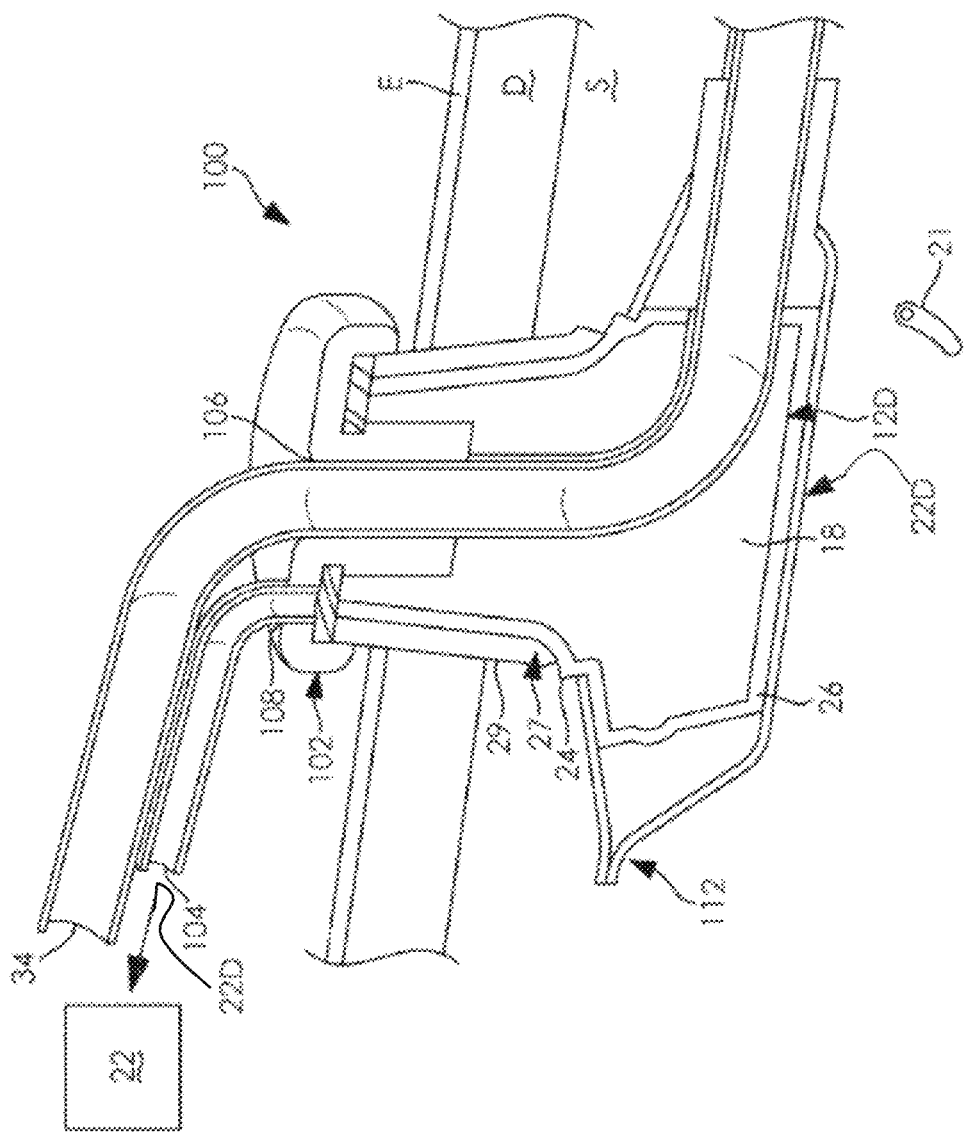
FIG. 1 is a prior art, partial cutaway view of a flanged percutaneous access device (PAD) with relative dimensions of aspect exaggerated for visual clarity.

FIG. 6A is an inventive embodiment of a modular external interface 300 configured to be coupled to the neck of an access device, where the access devices illustratively include a PAD such as the PAD 100 described in FIG. 1. The modular external interface 300 forms a seal with aperture 330 around a cylindrical neck of an access device, where the seal is enhanced by an applied vacuum through vacuum line 222. It should be appreciated that other geometries besides a circle for a neck extending from an access device may be accommodated, illustratively including a square, rectangle, triangle, or oval. In a specific embodiment the main body 316 is made of silicon and is placed over a foam layer 326, and the top outer surface of the main body 316 may have a layout line to provide guidance for placement of a securing medical dressing illustratively including Tegaderm™. The medical dressing is placed over the modular external interface 300 and attached to the subject's skin. The oval like shape and tapered sides 332 of the main body 316, which has no concavities, is configured to prevent wrinkling of the medical dressing where the main body 316, foam layer 326, and the subject's skin meet. The foam layer 326 may extend up to or just past the border of the tapered sides 332 of the main body 316. The foam layer 326 compacts and lowers the main body 316 over an implant or access device neck. Slit 334 in the main body 316 is provided to fit the modular external interface 300 around the neck of the implant or access device.

As best shown in FIG. 6B, the bottom perspective view with the foam layer 326 in transparent relief, a vacuum channel 328 is in fluid communication with vacuum attachment portal 324 for the vacuum line 222. The larger foam piece that forms the foam layer 326 moves the vacuum line entrance at the attachment portal 324 further away from the drive line that is inserted through aperture 330 and into the neck of the access device. In addition, the vacuum channel 328 of main body 316 is moved out radially from the neck of the implant/access device as compared to the main body 216 of modular external interface 200 as shown in side by side comparison in FIGS. 11A and 11B.

Figure 7A:
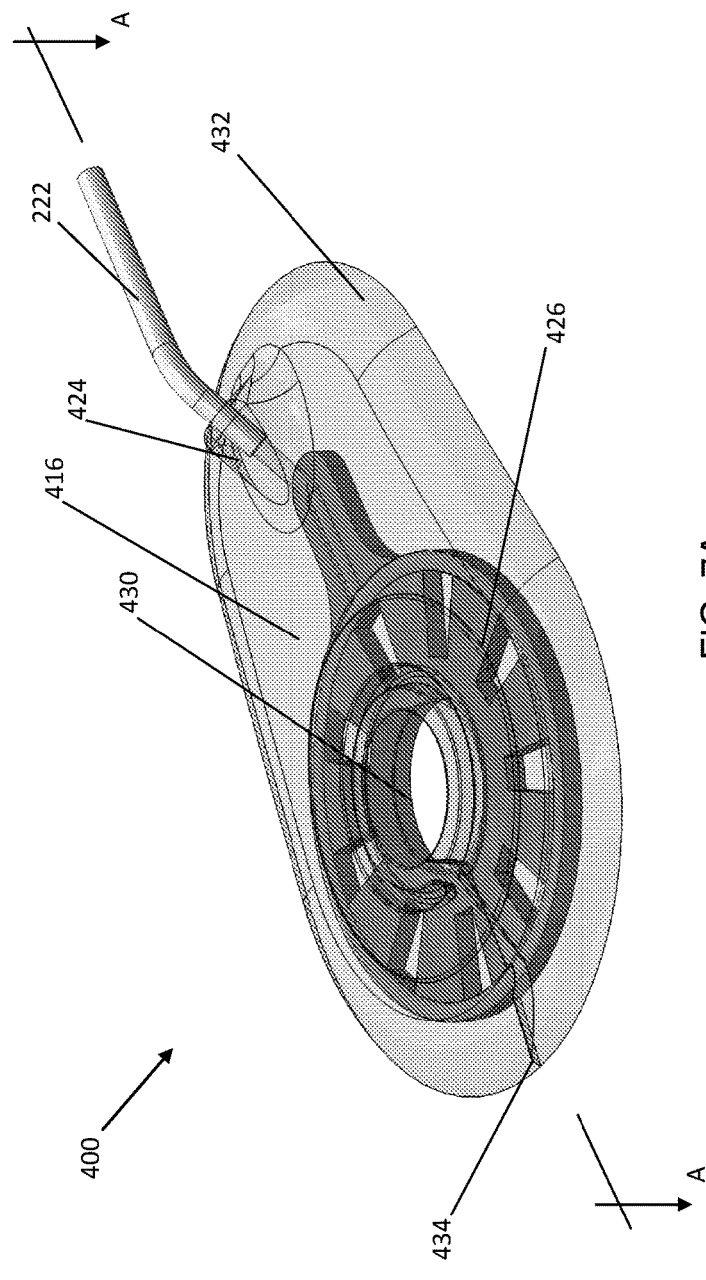
FIG. 7A is a perspective view of a modular external interface with a star or spoke foam insert.
Figure 7B:
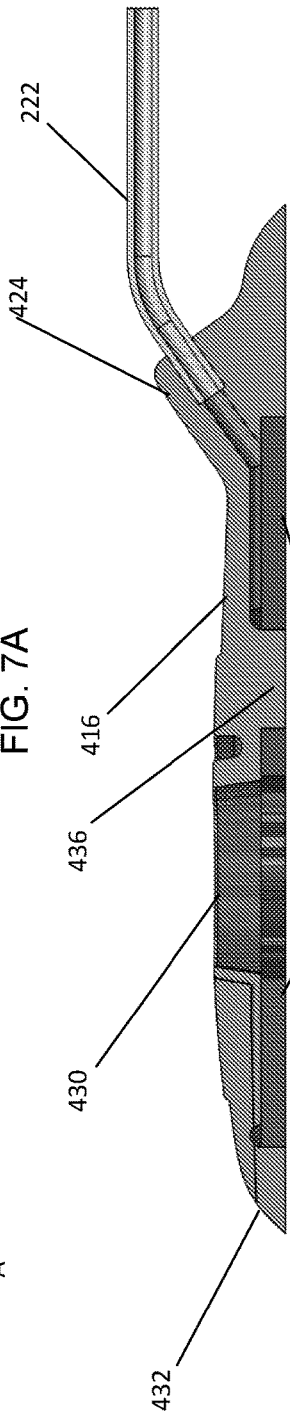
FIG. 7B is a cross-sectioned view of FIG. 7A in accordance with an embodiment of the invention.

FIG. 7A is an inventive embodiment of a modular external interface 400 configured to be coupled to the neck of an access device. Main body 416, which may be made of silicone in a specific embodiment, has support ribs 436 which support the skin from prolapsing. A foam insert 426 has a star shape to accommodate the support ribs 436. The foam insert in a specific embodiment may also have a circular circumference to support the subject's skin from the vacuum path. The modular external interface 400 forms a seal with aperture 430 around a cylindrical neck of an access device, where the seal is enhanced by an applied vacuum through vacuum line 222 that inserts into vacuum attachment portal 424. It should be appreciated that other geometries besides a circle for a neck extending from an access device may be accommodated, illustratively including a square, rectangle, triangle, or oval. The oval like shape and tapered sides 432 of the main body 416, which has no concavities, is configured to prevent wrinkling of the medical dressing where the main body 416 and the subject's skin meet. FIG. 7B is a cross-sectional view along line A-A of FIG. 7A.

FIGS. 8A and 8B illustrate a simple slit 334 for the modular external interface 300 of FIG. 6A. In embodiments of the modular external interface 300 with a simple slit 334, the securing medical dressing holds the halves of the modular external interface 300 together. In a specific embodiment, a transfer tape that is designed to adhere to silicone surfaces may be used for a stronger and more secure holding of the halves together. FIGS. 9A and 9B illustrate a simple slanted slit 336 for the modular external interface 300 of FIG. 6A. The slant in slit 336 allows for two sides of main body 316' to spread apart and still seal to one another, where opposing sides at the slant slit 336 overlap. In a similar manner, the slant in the slit 336 may utilize a transfer tape that is designed to adhere to silicone surfaces, and the tape may be used for a stronger and more secure holding of the halves joined together with the slanted slit 336.

Figure 10B:
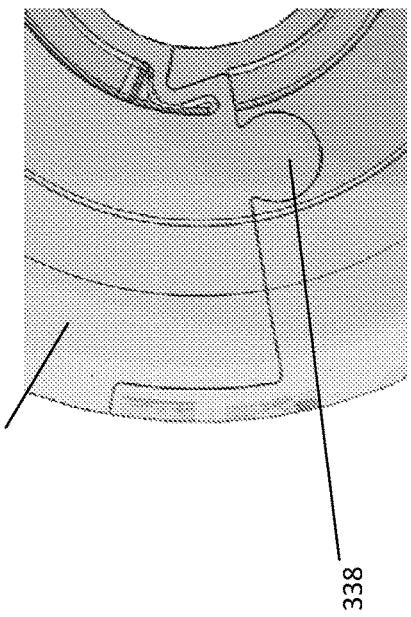
FIGS. 10A and 10B are perspective views of a modular external interface seal with a locking feature in accordance with an embodiment of the invention.
Figure 10A:
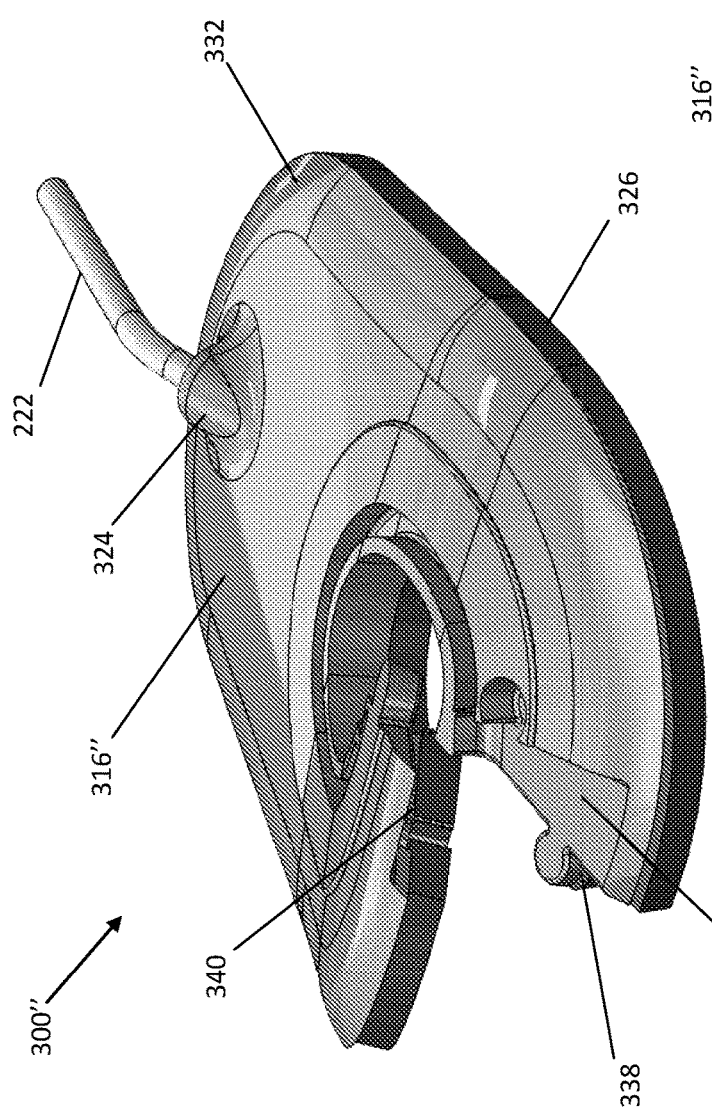

FIGS. 10A and 10B illustrate a modular external interface 300" that forms a collar about the neck 110 of the PAD 100 with the main body 316" with a locking feature 338, such as a male extension that engages a female receptacle or cavity as a mechanical overlap connection in a tongue 340 and groove 342 configuration. The puzzle like configuration of the locking feature 338 is also formed in the foam layer 326, and keeps the foam 326 and the main body from pulling apart.

Figure 13A:
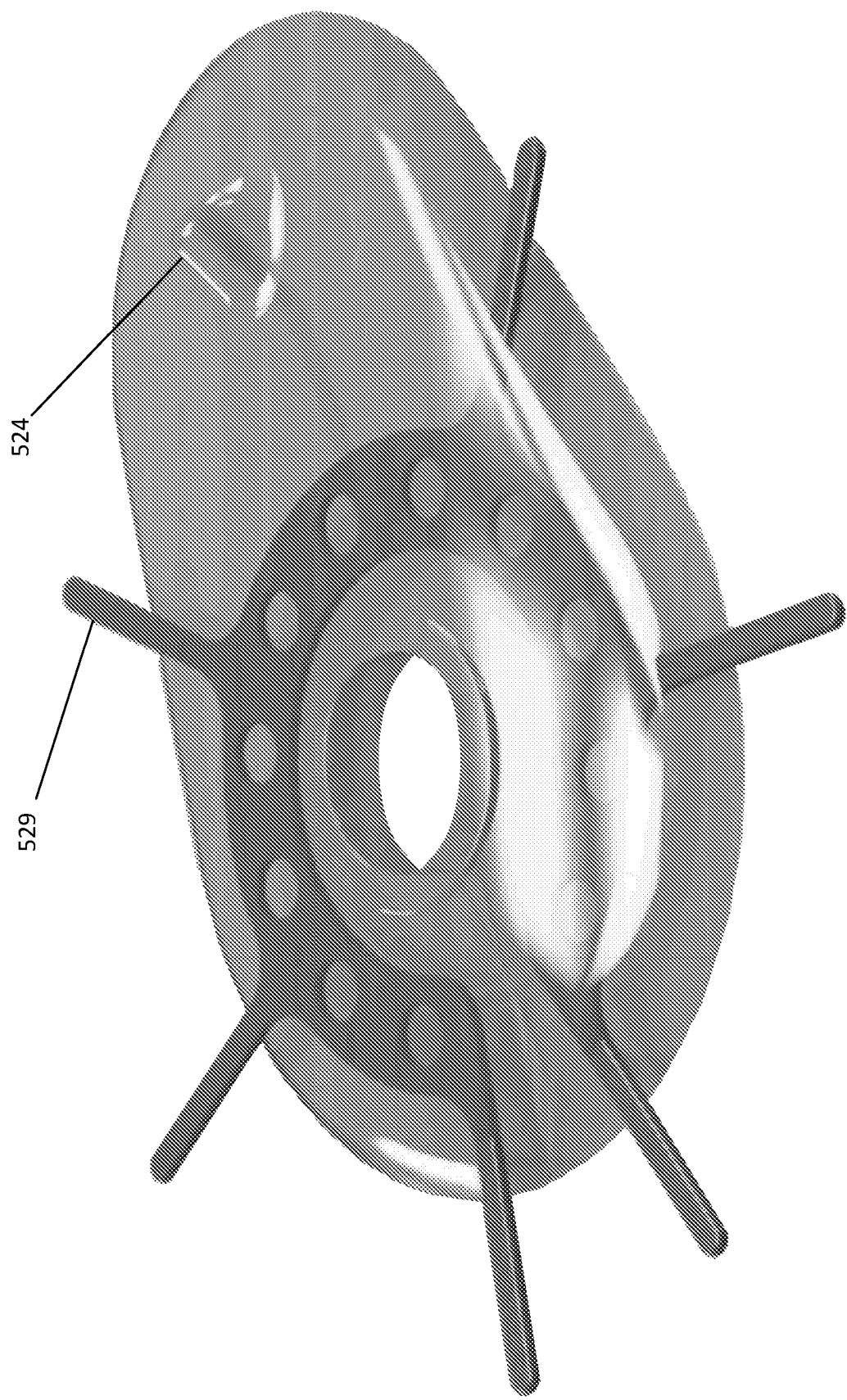
FIGS. 13A-13C are perspective views of the main body portion of a modular external interface seal in accordance with an embodiment of the invention.
Figure 13B:
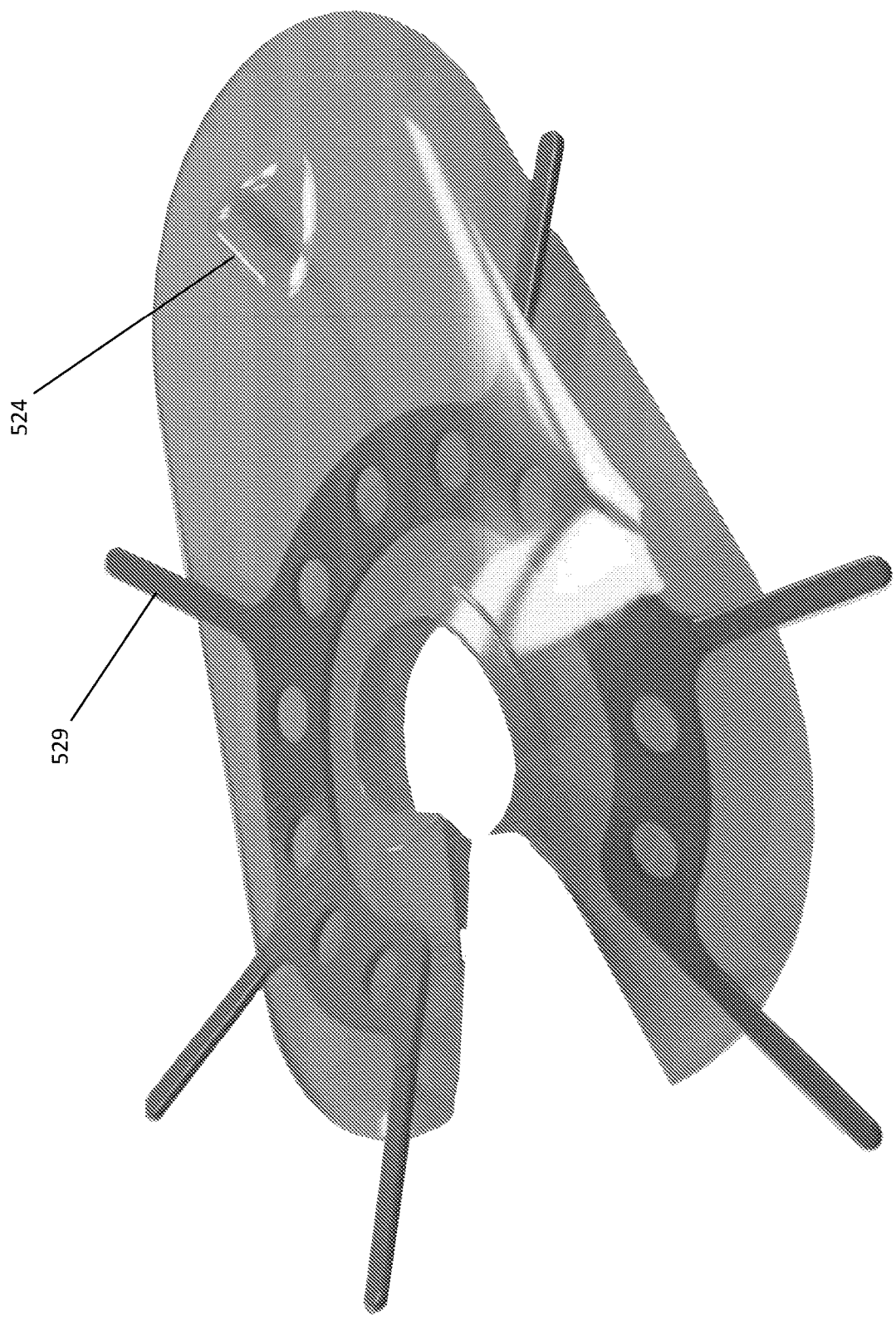
Figure 13C:
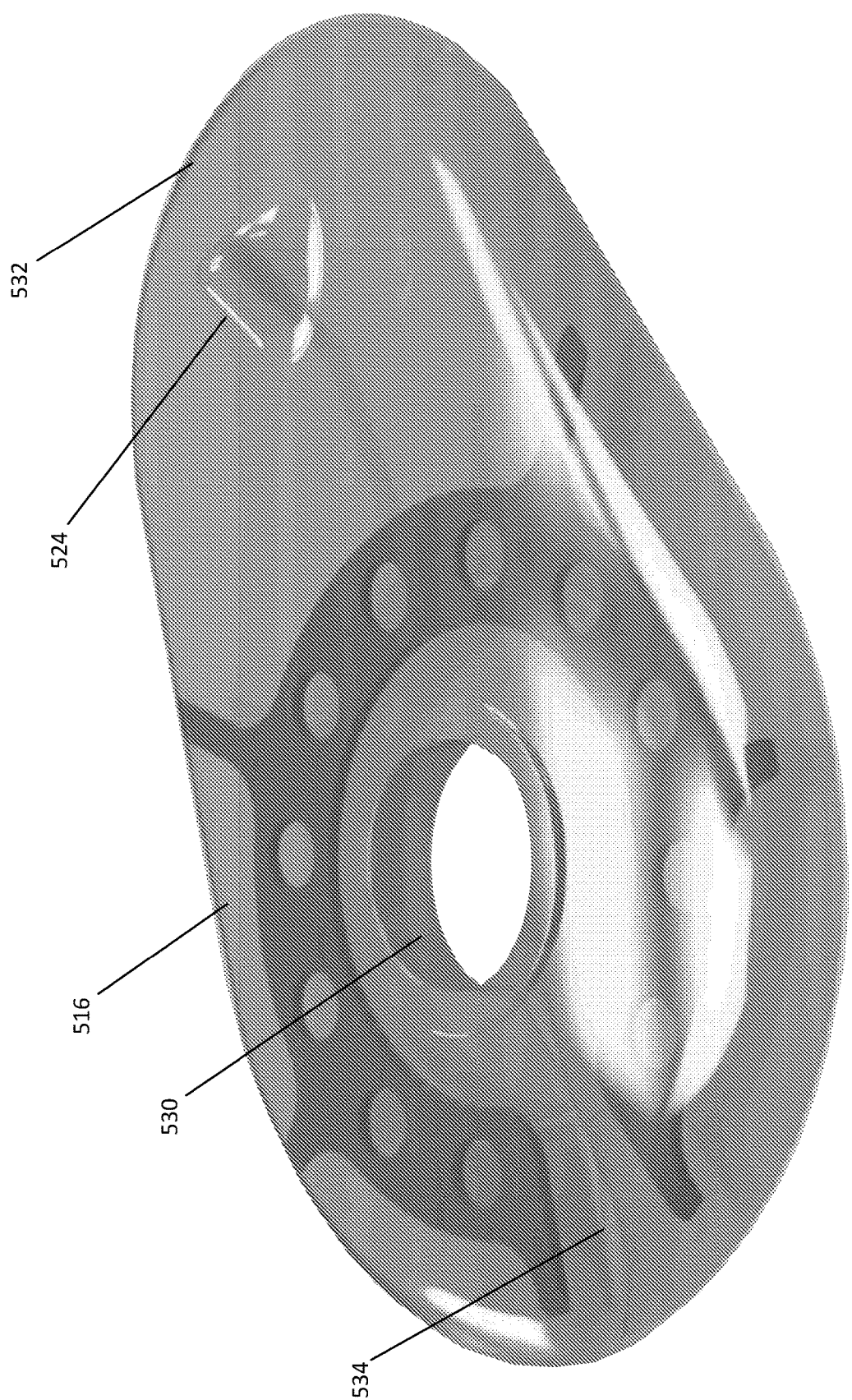
Figure 14:
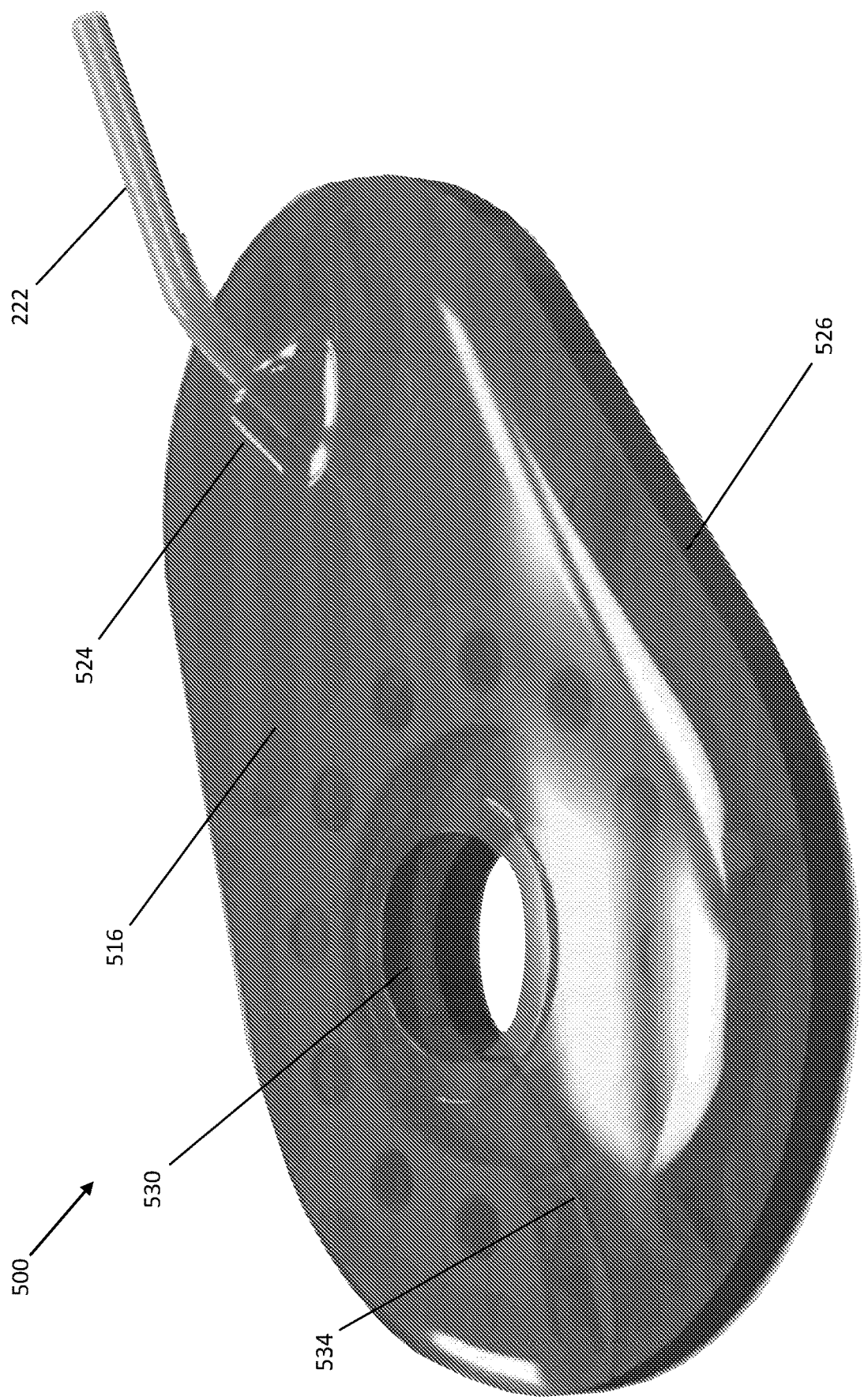
FIG. 14 is a perspective view of a modular external interface seal in accordance with an embodiment of the invention.
Figure 15:
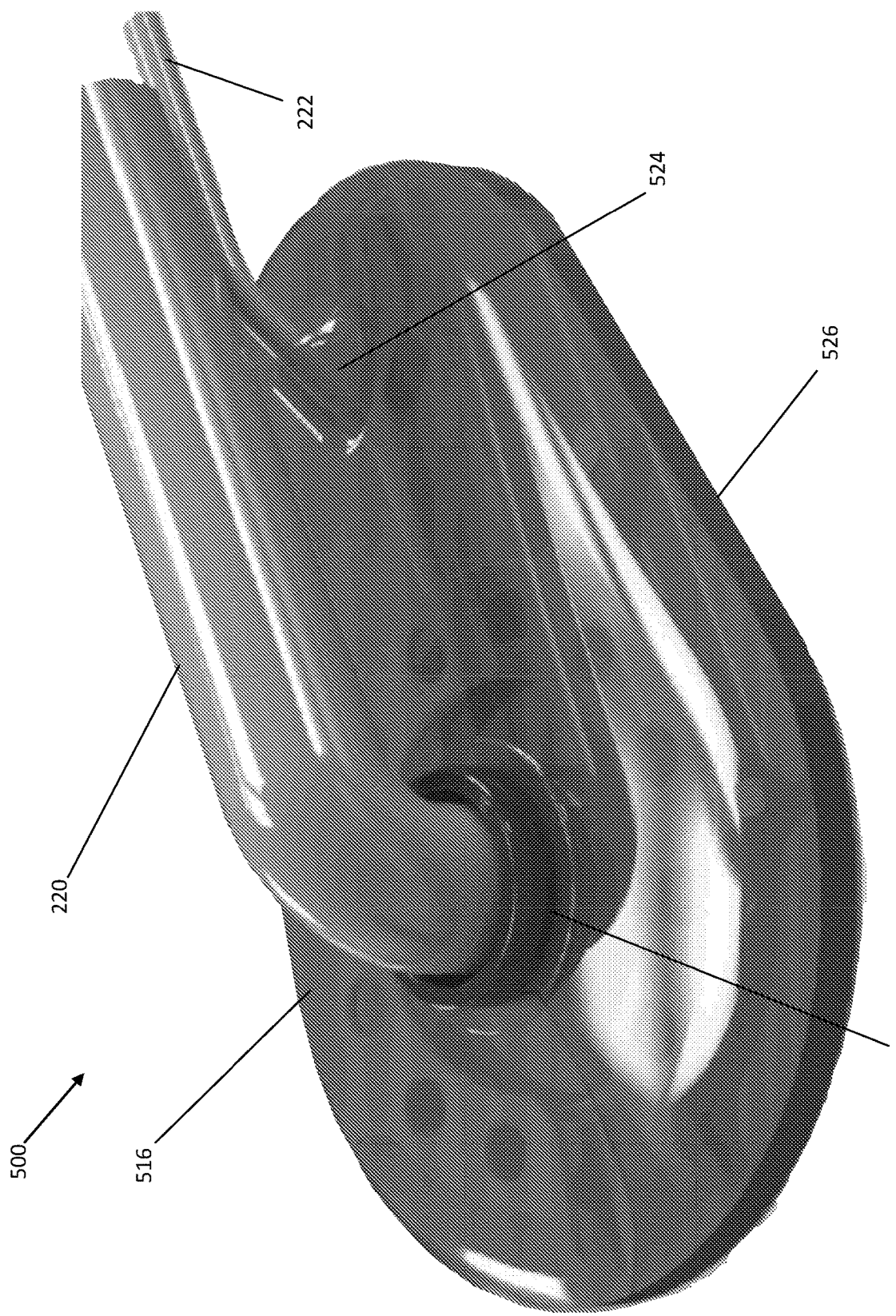
FIG. 15 is a perspective view of a modular external interface seal joined about a skin-appliance interface in accordance with an embodiment of the invention.

FIG. 15 is an inventive embodiment of a modular external interface 500 configured to be coupled to the neck of an access device, where the access devices illustratively include a PAD such as the PAD 100 described in FIG. 1. FIG. 14 illustrates the modular external interface 500 prior to positioning about the neck of an access device. The modular external interface 500 forms a seal with aperture 530 around a cylindrical neck 110 of an access device, where the seal is enhanced by an applied vacuum through vacuum line 222 attached to the modular external interface 500 via vacuum attachment portal 524. It should be appreciated that other geometries besides a circle for a neck extending from an access device may be accommodated, illustratively including a square, rectangle, triangle, or oval. It should be noted that in FIGS. 13-15 the main body 516 is shown as transparent, but in other embodiments the main body may be translucent. In a specific embodiment the main body 516 is made of silicon and is placed over a foam layer 526, and the top outer surface of the main body 516 may have a layout line to provide guidance for placement of a securing medical dressing illustratively including Tegaderm™. The medical dressing is placed over the modular external interface 500 and attached to the subject's skin. The oval like shape and tapered sides or edges 532 of the main body 516, which has no concavities, is configured to prevent wrinkling of the medical dressing where the main body 516, foam layer 526, and the subject's skin meet. The foam layer 526 may extend up to or just past the border of the tapered sides 532 of the main body 516. The foam layer 526 compacts and lowers the main body 516 over an implant or access device neck. Slit 534 in the main body 516 is provided to fit the modular external interface 500 around the neck of the implant or access device. FIG. 13B illustrates the main body 516 with the slit 534 separated for placement around the neck of the implant or access device.

Figure 12A:
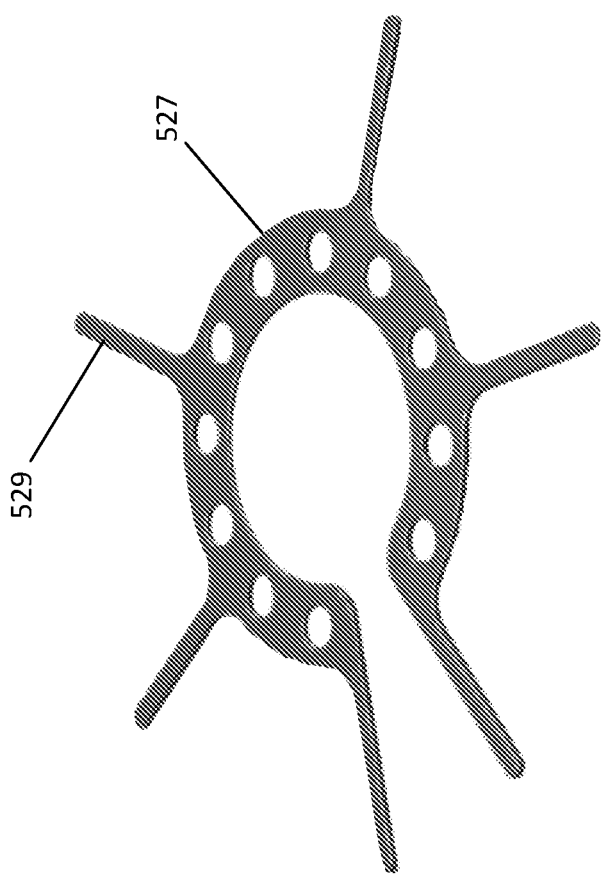
FIGS. 12A and 12B are perspective views of a support foam insert for use with a modular external interface seal in accordance with an embodiment of the invention.
Figure 12B:
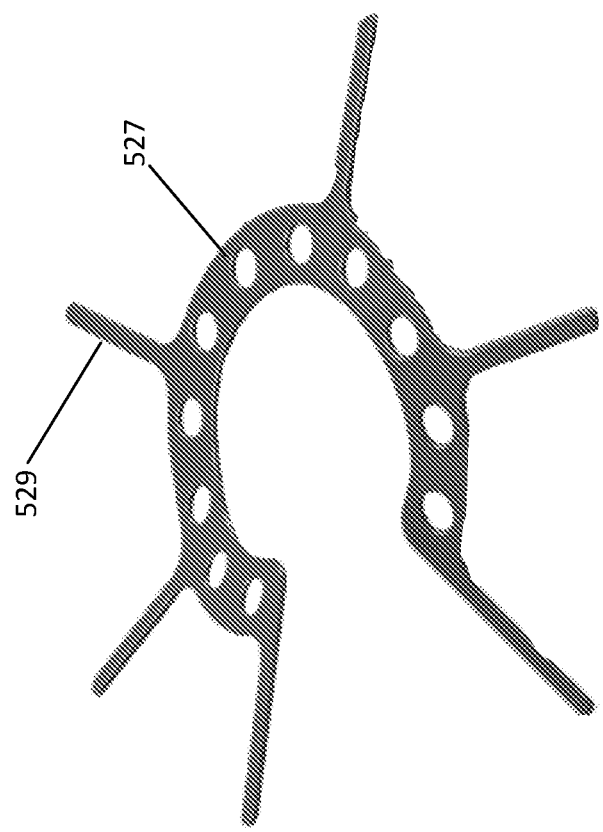

In a specific embodiment, the main body 516 has support ribs which support the skin from prolapsing. A support foam insert 527 as shown in FIGS. 12A and 12B has a rounded shape with branches or arms 529 protruding radially outward to accommodate the support ribs. The protruding arms 529 are configured to be inserted in channels in the main body 516, as best shown in FIGS. 13A-13C, where excess length of the protruding arms 529 are trimmed off in FIG. 13C.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A modular external interface comprising:
   a main body having an external surface and defining an aperture;
   a portal on said main body having an insertion channel parallel to the external surface of said main body;
   at least one driveline having a first portion and a second portion connected by an elbow, said second portion of said at least one driveline inserted through said aperture; and
   a medical dressing;
   wherein said aperture is configured to form a collar seal about an external neck portion of a skin penetrating appliance;
   wherein said portal is configured for insertion of a straight vacuum tube in line with said insertion channel;
   wherein said medical dressing is configured to cover the external surface of said main body and secure and seal said main body to an outer layer of a patient's skin;
   wherein said second portion of said at least one driveline is further inserted through said aperture and into the external neck of the skin penetrating appliance;
   wherein said first portion of said at least one driveline and said straight vacuum tube are parallel to the outer layer of the patient's skin; and
   wherein said straight vacuum tube is positioned a first distance from the external surface of said main body and said first portion of said at least one driveline is positioned a second distance from the external surface of said main body, the second distance being greater than the first distance.

2. The interface of claim 1 wherein said main body is made of silicone.

3. The interface of claim 1 wherein said collar seal is formed with a gasket positioned between the external neck of the skin penetrating appliance and said aperture of said modular external interface.

4. The interface of claim 1 wherein said main body is transparent or translucent.

5. The interface of claim 1 further comprising a locking feature to secure said main body to the external neck of the skin penetrating appliance.

6. The interface of claim 1 further comprising a locking feature to secure said main body to the external neck of the skin penetrating appliance; and
wherein said locking feature further comprises a male extension that engages a female receptacle or cavity as a mechanical overlap connection in a tongue and groove configuration.

7. The interface of claim 1 further comprising a skin protection layer positioned inside said main body and adjacent to the patient's skin; and a foam disc above said skin protection layer.

8. The interface of claim 1 wherein said medical dressing is a preform made in two overlapping halves.

9. The interface of claim 1 wherein said medical dressing is transparent.

10. The interface of claim 1 further comprising a slit in said main body that is provided to fit said modular external interface around the external neck of the skin penetrating appliance.

11. The interface of claim 10 wherein said slit is slanted, and a set of opposing sides of said main body are formed by overlapping of said slit.

12. A modular external interface comprising:
a main body having a bottom surface and defining an aperture, the bottom surface defining a vacuum channel, the aperture configured to form a collar seal about an external neck portion of a skin penetrating appliance, where a slit extends outward from said aperture;
a portal on said main body having an insertion channel parallel to the external surface of said main body, said insertion channel configured for insertion of a straight vacuum tube in line with said insertion channel, where the portal is in fluid communication with the vacuum channel defined in the bottom surface of said main body;
a foam layer configured to be positioned under said main body in contact with the bottom surface of said main body;
at least one driveline having a first portion and a second portion connected by an elbow, said second portion of said at least one driveline inserted through said aperture and into the external neck of the skin penetrating appliance;
wherein said second portions of said at least one driveline and said straight vacuum tube are parallel to an outer layer of a patient's skin to which said modular external interface is applied; and
wherein said straight vacuum tube is positioned a first distance from the external surface of said main body and said first portion of said at least one driveline is positioned a second distance from the external surface of said main body, the second distance being greater than the first distance.

13. The interface of claim 12 wherein said main body is made of silicone.

14. The interface of claim 12 further comprising a locking feature to secure said main body to the external neck of the skin penetrating appliance.

15. The interface of claim 12 wherein said main body is transparent or translucent.

16. The interface of claim 12 wherein said main body has tapered sides.

17. The interface of claim 12 wherein said slit is slanted with overlapping halves.

18. The interface of claim 12 further comprising a medical dressing configured to cover an external surface of said main body and secure and seal said main body to an outer layer of a patient's skin.

19. A process of using the modular external interface of claim 1 comprising:
placing the modular external interface over an external neck portion of a skin penetrating appliance implanted in a subject; and
applying the medical dressing to the external surface of the main body to secure and seal the main body to an outer layer of a subject's skin.

20. The interface of claim 1 wherein said portal is raised or protrudes above said main body.

21. The interface of claim 12 wherein said portal is raised or protrudes above said main body.

* * * * *